(12) United States Patent
Gajanan et al.

(10) Patent No.: US 8,722,071 B2
(45) Date of Patent: May 13, 2014

(54) MICROCAPSULES CONTAINING BIOCIDE AND PREPARATION THEREOF BY SOLVENT EVAPORATION TECHNIQUE

(75) Inventors: Shukla Parshuram Gajanan, Pune (IN); Swaminathan Sivaram, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 1488 days.

(21) Appl. No.: 11/363,547

(22) Filed: Feb. 27, 2006

(65) Prior Publication Data

US 2006/0246144 A1 Nov. 2, 2006

(30) Foreign Application Priority Data

Feb. 28, 2005 (IN) .............................. 426/DEL/2005

(51) Int. Cl.
*A01N 25/28* (2006.01)
*A01N 25/12* (2006.01)
*A01N 43/66* (2006.01)

(52) U.S. Cl.
USPC ........................... 424/408; 424/405; 514/245

(58) Field of Classification Search
None
See application file for complete search history.

(56) References Cited

U.S. PATENT DOCUMENTS

| 4,253,877 | A | 3/1981 | Miale et al. | |
|---|---|---|---|---|
| 4,915,947 | A | 4/1990 | Thenard et al. | |
| 5,378,413 | A | 1/1995 | Mihm et al. | |
| 5,725,869 | A | 3/1998 | Lo | |
| 5,955,096 | A | * | 9/1999 | Santos et al. .................. 424/434 |
| 2004/0234603 | A1 | 11/2004 | Baum et al. | |
| 2007/0053950 | A1 | 3/2007 | Gajanan et al. | |

FOREIGN PATENT DOCUMENTS

| EP | 679333 | 11/1995 |
|---|---|---|
| JP | 2003104802 | 4/2003 |

OTHER PUBLICATIONS

Microspheres, Microcapsules, and Liposomes, vol. 1, Arshady (editor), Citus Books, London, UK, 1999.
"Evaluation of an aliphatic polyurethane as a microsphere matrix for sustained theophylline delivery", Subhaga et al., J. Microencapsulation, 1995, vol. 12, No. 6, 617-625.
"Oil Core/Polymer Shell Microcapsules by Internal Phase Separation from Emulsion Droplets. II: Controlling the Release Profile of Active Molecules," Dowding et al. Langmuir 2005, 21, 5278-5284.
"Polyanhydride microspheres: 3. Morphology and characterization of systems made by solvent removal," Mathiowitz et al. Polymer, 1990, vol. 31, March.
"Solute and Penetrant Diffusion in Swellable polymers IV. Semicrystalline, swelling-controlled release systems of poly (ethylene-co-vinyl alcohol)" Segot-Chicq et al., Journal of Controlled Release, 3, (1986), 193-204.
"Influence of coating and core modifications on the in vitro release of methylene blue from ethylcellulose microcapsules produced by a pan coating procedure" Brophy et al., J. Pharm. Pharmcol. 1981, 33: 495-499.

* cited by examiner

*Primary Examiner* — Daniel Sullivan
*Assistant Examiner* — Barbara Frazier
(74) *Attorney, Agent, or Firm* — Meyertons, Hood, Kivlin, Kowert & Goetzel, P.C.; Eric B. Meyertons

(57) ABSTRACT

The present invention provides polymer microcapsules of biocide, useful for preparing coating materials such as interior and exterior paints, which comprises of an active agent biocide and an encapsulating polymer. Microcapsules described in this invention are prepared by dispersing an organic phase containing an active agent either in dissolved state or dispersed state in a polymer solution using a low boiling point solvent, in an aqueous phase containing an emulsifying agent; agitating the emulsion at 800-1200 resolution per minute for 3-5 hours at 25 -27° C. to evaporate the low boiling point solvent and thus to permit the formation of the microcapsules; separating the microcapsules, washing with water and drying the microcapsules at temperature between 25-35° C.

23 Claims, No Drawings

MICROCAPSULES CONTAINING BIOCIDE AND PREPARATION THEREOF BY SOLVENT EVAPORATION TECHNIQUE

FIELD OF THE INVENTION

This invention relates to polymer microcapsules containing biocide selected from Zinc Pyrithione and Irgarol and a process for the preparation thereof.
More particularly, the present invention relates to polymer microcapsules of Zinc Pyrithione and Irgarol having the controlled particle size of 1-100 microns and a process for the preparation thereof by solvent evaporation technique.

BACKGROUND OF THE INVENTION

Biocides are chemical compounds, which are toxic to microbial cells and are added to different types of products to prevent the growth of unwanted microorganisms. Reduction in biocidal activity is mostly attributed to the factors such as chemical degradation of biocide, fast dissipation of biocide from application site due to washing out and/or volatilization. The life of any product where biocide is applied, will be more if these biocides are retained in the product/application site for longer period. This extended duration of biocidal activity can be achieved by incorporating biocide in Controlled Release (CR) form. Microcapsule is one of the best controlled release form, wherein an active agent (core material) is surrounded by a polymer film. This is achieved by a process called microencapsulation. Different techniques of microencapsulation are known which include phase separation, solvent evaporation, interfacial polymerization and mechanical methods such as spray drying.

Numbers of reviews on microencapsulation techniques have appeared in literature. (i) Arshady R. (Editor), Microspheres, Microcapsules and Liposomes, Vol. 1 and 2, 1999 and Vol. 6, 2003 Citus Book, UK (ii) Benita S. (Editor), Microencapsulation-Methods and Industrial Applications, 1996, Marcel Dekker Inc., New York; (iii) Madan P. L., Asian J. Pharm. Sci., 9, 1979, p 1; (iv) Thies C. In: Encyclopedia of Polymer Science and Engineering, Vol. 9, Wiley & Sons, New York, 1987, p 724 and (v) Porte H. and Couarrze G., In: Hand book of Powder Technology, 9 (Powder Technology and Pharm. Processes) 1994, p 513). U.S. patents disclosing various microencapsulation methods have been consolidated (Gutcho M. 'Microcapsules and Microencapsulation Techniques'. New York, Noyes Data, 1976).
Controlled Release Biocides:

Controlled Release (CR) biocides has been the subject of interest to many researchers. CR concept and work was initiated first time on antifouling paints using chloroprene polymer by Prof. N. F. Cardarelli (Cardarelli N. F., Chapter 3 In Controlled Release Technologies: Methods, Theory & Applications, Ed. Kydonieus A. F., 1980, CRC Press Inc., USA). Antifouling marine paint composition containing gelation microcapsules of water-immiscible biocide has been described in U.S. Pat. No. 4,253,877. Yet another U.S. Pat. No. 5,378,413 describes preparation of gelatin microcapsules containing fouling reducing agents and their use in paint system. Another report describes extended control of marine fouling using formulation of microencapsulated organometallic biocide and vinyl rosin paint. (Porter R. and Miale J. B., Appl. Biochem. and Biotech., 9 (1984), p 439-445 (CA 102: 162052)).

Apart from CR antifouling formulations there have been very few reports on CR of other biocides. Biocide namely 4,5-dichloro-n-octyl-3-isothiazolinone (DCOI) can be encapsulated in a variety of polysiloxane matrices using sol-gel chemistry (Ghosh T. and Nungesser E. N., Proc. Int. Symp. Control. Rel. Bioact. Mater. 25 (1998), p 324). The skin sensitization potential of active agent (3-isothiazolone) in loci such as water-based marine antifouling paint of decorative is reduced by encapsulating the active agent in polyurea (.EP 679333 (1995), (CA 123: 332738)). The fungicide tebuconazole and chlorothalonil were successfully incorporated into polyvinylpyridine (PVPy) and polyvinylpyridine-co-styrene nano particles (Liu Y. et. al., J. Appl. Poly. Sci, 79 (2001), p 458-465).

U.S. Pat. No. 4,915,947 describes preparation of microencapsulated phytotoxic fungicides using crosslinked polytirea or polyamide to provide an effective agent for direct foliar application to control fungal diseases on crops. Urea-formaldehyde (UF) and/or melamine formaldehyde (MF) resins have been used to prepare microcapsules of fungicide namely 3-Iodo-2-propynylbutyl carbamate. These microcapsules when incorporated into exterior latex paint and applied onto rubberwood panels on exposing to the environment showed longer protection from discoloration. (Ibrahim W. A. et. al., Pertanika 12 (1989) p 409-412 (CA 114:25832)). The acrylic latex exterior paint containing microcapsules of fungicides 2,3,5,6-tetrachloro-4-methylsulfonylpryidine and tetrachloroisophthaonitrile have been reported to show good mildew protection (Noren G. K. et. al., J. Coatings Tech. 58 (1986), p 31-39 (CA 104: 188225)).

Another patent describes encapsulation of biocide using MF resin and their use in coating material like plaster having silicate, mineral or polymer resin binder or a primer based on a silicate or polymer resin binder (Patent WO 2004000953). The patent describes preparation of microcapsules containing Zinc Pyrithione using MF resin but does not specify the size of the microcapsules obtained. Japanese patent (No. JP 2003104802) describes antibacterial aqueous dispersion compositions containing microencapsulated dithioles or 2,2-dibromo-3-nitrilopropionamide and other microbiocides like Zinc Pyrithione. The patent does not describe preparation of microcapsules of Zinc Pyrithione but mentions that Zinc Pyrithione is added to composition containing microcapsules of other compounds as mentioned above.
Microcapsules Prepared by Solvent Evaporation:

There are many reports in the literature related to preparation of microcapsules by solvent evaporation techniques. These reports are documented in the references mentioned in the introduction part of the section "Prior art references and background of the invention". Microencapsulation by solvent evaporation is carried out involving oil in water, water in oil or water in oil in water type emulsion systems.

U.S. Pat. No. 5,725,869 describes preparation of microcapsules containing agricultural materials by solvent evaporation method. Microcapsules described in this patent have a size of between about 3 and about 300 microns in diameter. The complex water in oil in water or simple water in oil emulsion system has been used to prepare polystyrene, poly(methyl methacrylate), ethyl cellulose, poly(vinyl chloride) microcapsules containing aqueous solution of gelatin (Kentepozidou A. and Kiparissides C. J. Microencapsulation 12 (1995) p 627-638). Solvent evaporation method involving such double emulsion system (water in oil in water) has been used to prepare microcapsules of polystyrene containing corrosion inhibitors (Anne Mac et al., J. Microencapsulation 6 (1989) p 361-367) poly(methyl methacrylate) microcapsules containing highly water soluble drug (Alex R. and Bodmeier R., J. Microencapsulation 7 (1990) p 347-355) or water soluble dyes (Zydowicz N. et al., Poly. Bull. 47 (2002) p 457-463, CA 136:341624).

Biocides play an important role in variety of applications. However reduction in biocidal activity due to factors such as chemical degradation of biocide and/or fast dissipation of biocide from the application site due to reasons like washing out with water is a problem which leads to decrease in period of effectiveness of biocide.

In the prior art there is no existence of any product like polymer microcapsules of biocide selected from Irgarol and Zinc Pyrithione particularly with specified particle size or size range.

Thus to satisfy the need to prolong the life of biocide, present invention provides microcapsules of Irgarol and Zinc Pyrithione with controlled particle size distribution in the range of 1-100 microns, which are effective algaecide and fungicide respectively.

OBJECTIVES OF THE INVENTION

The main object of the present invention is to provide polymer microcapsules of biocide selected from Irgarol and Zinc Pyrithione using polymer selected from polystyrene and poly(methyl methacrylate) in particular.

Another object of the present invention is to provide a process for the preparation of polymer microcapsules of Irgarol and Zinc Pyrithione, having controlled particle size distribution in the range of 1-100 microns and preferably between 2-50 microns.

SUMMARY OF THE INVENTION

Accordingly the present invention provides polymer microcapsules containing biocide selected from Irgarol and Zinc Pyrithione having particle size distribution in the range of 5-100 microns.

In an embodiment of the present invention the encapsulating polymer used is selected from a group consisting of poly (methyl methacrylate), polystyrene, copolymer such as poly (vinylpyridine-co-styrene) and organic polymer such as ethyl cellulose.

In yet another embodiment the ratio of biocide to polymer used is in the range of 0.25 to 1.0.

In yet another embodiment the particle size of microcapsules obtained is preferably in the range of 5-50 microns.

The present invention, further provides a process for the preparation of microcapsules of biocide selected from Irgarol and Zinc Pyrithione, which comprises dispersing an organic phase containing biocide either in dissolved or dispersed state in a polymer solution using a low boiling point solvent, in an aqueous phase containing an emulsifying agent; agitating the above said emulsion at a speed of 800-1200 rpm, for a period of 4-6 hrs, at a temperature of 25-27° C. to evaporate the low boiling point organic solvent to obtain the resultant microcapsules of biocide, separating and washing the resultant product with water followed by drying at a temperature ranging between 25-35° C. to obtain the desired controlled particle size of polymer microcapsules.

In an embodiment of the present invention the organic phase used is prepared by dissolving polymer in a water immiscible, low boiling organic solvent.

In yet another embodiment the low boiling organic solvent used for preparing an organic phase is selected from the group consisting of dichloromethane, chloroform and ethyl acetate.

In yet another embodiment the concentration of polymer used in organic phase is in the range of 3 to 20 w/v %.

In yet another embodiment the concentration of biocide used in organic phase is in the range of 2 to 20 w/v %.

In yet another embodiment the emulsifying agent used in aqueous phase is poly(vinyl alcohol).

In yet another embodiment the amount of emulsifying agent used in aqueous phase is in the range of 1 to 8 w/v % having degree of hydrolysis of 80-98%.

In yet another embodiment the ratio of organic phase to aqueous phase used is in the range of 1:5 to 1:20.

In yet another embodiment the evaporation of solvent occurs either in an open system in a fume hood at an atmospheric pressure or in a closed system, at reduced pressure.

In still another embodiment the aggregation of microcapsules obtained and presence of free biocide is avoided by adding an appropriate amount of water to the aqueous phase after complete addition of organic phase to aqueous phase.

DETAIL DESCRIPTION OF THE INVENTION

The present invention provides polymer microcapsules of biocide, useful for preparing coating materials such as interior and exterior paints, which comprises of an active agent biocide and an encapsulating polymer. Microcapsules described in this invention are prepared by dispersing an organic phase containing an active agent either in dissolved state or dispersed state in a polymer solution using a low boiling point solvent, in an aqueous phase containing an emulsifying agent; agitating the emulsion at 800-1200 resolution per minute for 3-5 hours at 25-27° C. to evaporate the low boiling point solvent and thus to permit the formation of the microcapsules; separating the microcapsules, washing with water and drying the microcapsules at temperature between 25-35° C. This invention is further illustrated by the following examples which should not be construed to limit the scope of the invention.

EXAMPLE 1

Aqueous phase is prepared by dissolving 2 g of polyvinyl alcohol in 100 mL distilled water by stirring and heating the mixture at 60-70° C. Organic phase is prepared by dissolving 1 g of polystyrene and 0.4 g of Irgarol in 20 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered, washed with distilled water and vacuum dried at 25-27° C. for 3-4 hours. The yield of the product is 1.28 g. Microcapsules have particle size range of 5-65 microns of which a majority of particles are 20-35 microns.

EXAMPLE 2

Aqueous phase is prepared by dissolving 2 g of polyvinyl alcohol in 100 mL distilled water by stirring and heating the mixture at 60-70° C. Organic phase is prepared by dissolving 1 g of polystyrene and 0.4 g of Irgarol in 10 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered, washed with distilled water and vacuum dried at 25-27° C. for 3-4 hours. The yield of the product is 1.32 g. Microcapsules have particle size range of 5-55 microns of which a majority of particles are 20-35 microns.

EXAMPLE 3

Aqueous phase is prepared by dissolving 3 g of polyvinyl alcohol in 100 mL distilled water by stirring and heating the mixture at 60-70° C. Organic phase is prepared by dissolving 1 g of polystyrene and 0.4 g of Irgarol in 20 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 1.34 g. Microcapsules have particle size range of 2-25 microns of which a majority of particles are 10-20 microns.

EXAMPLE 4

Aqueous phase is prepared by dissolving 20 g of polyvinyl alcohol in 500 mL distilled water by stirring and heating the mixture at 60-70° C. Organic phase is prepared by dissolving 5 g of polystyrene and 2 g of Irgarol in 100 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 6.7 g. Microcapsules have particle size range of 2-40 microns of which a majority of particles are 10-25 microns.

EXAMPLE 5

Aqueous phase is prepared by dissolving 3 g of polyvinyl alcohol in 100 mL distilled water by stirring and heating the mixture at 60-70° C. Organic phase is prepared by dissolving 1 g of polystyrene and 0.8 g of Irgarol in 20 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 1.72 g. Microcapsules have particle size range of 2-30 microns of which a majority of particles are 10-20 microns.

EXAMPLE 6

Aqueous phase is prepared by dissolving 2 g of polyvinyl alcohol in 100 mL distilled water by stirring and heating the mixture at 60-70° C. Organic phase is prepared by dissolving 1 g of polystyrene and 0.4 g of Zinc Pyrithione in 20 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 1.26 g. Microcapsules have particle size range of 5-65 microns of which a majority of particles are 25-45 microns.

EXAMPLE 7

Aqueous phase is prepared by dissolving 15 g of polyvinyl alcohol in 500 mL distilled water by stirring and heating the mixture at 60-70° C. Organic phase is prepared by dissolving 5 g of polystyrene and 4 g of Zinc Pyrithione in 100 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 8.2 g. Microcapsules have particle size range of 2-60 microns of which a majority of particles are 10-25 microns.

EXAMPLE 8

Aqueous phase is prepared by dissolving 6 g of polyvinyl alcohol in 200 mL distilled water by stirring and heating the mixture at 60-70° C. Organic phase is prepared by dissolving 2 g of poly(methyl metacrylate) and 0.8 g of Irgarol in 40 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 2.59 g. Microcapsules have particle size range of 2-40 microns of which a majority of particles are 5-20 microns.

EXAMPLE 9

Aqueous phase is prepared by dissolving 3 g of polyvinyl alcohol in 100 mL distilled water by stirring and heating the mixture at 60-70° C. Organic phase is prepared by dissolving 1 g of poly(methyl metacrylate) and 0.4 g of Zinc Pyrithione in 20 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 1.3 g. Microcapsules have particle size range of 5-60 microns of which a majority of particles are 10-20 microns.

EXAMPLE 10

Aqueous phase is prepared by dissolving 6 g of polyvinyl alcohol in 200 mL distilled water by stirring and heating the mixture at 60-70° C. Organic phase is prepared by dissolving 2 g of poly(methyl metacrylate) and 1.6 g of Zinc Pyrithione in 40 mL dichloromethane. This organic phase is then added drop wise to the aqueous phase being stirred by turbine type stirrer at 1000 rotations per minute in a fume hood at atmospheric pressure. Formation of foam was suppressed by adding few drops of octyl alcohol. After stirring the mixture for 4-5 hours obtained microcapsules are filtered washed with distilled water and vacuum dried at 25-27° C. for 3-4 hours. The yield of the product is 3.5 g. Microcapsules have particle size range of 5-60 microns of which a majority of particles are 10-20 microns.

Advantages

Biocides play an important role in variety of applications. However reduction in biocidal activity due to factors such as chemical degradation of biocide and/or fast dissipation of biocide from the application site due to reasons like washing out with water is a problem which leads to decrease in period of effectiveness of biocide. Microencapsulated biocide will prolong the life of biocide and being encapsulated in polymer will result in less environmental pollution which un-encapsulated biocide may cause.

We claim:

1. A process for the preparation of microcapsules comprising Irgarol, the method comprising dispersing an organic phase containing Irgarol either in dissolved or dispersed state in a polymer solution using a low boiling point solvent, in an aqueous phase containing an emulsifying agent; agitating the above said emulsion at a speed of 800-1200 rpm, for a period of 4-6 hrs, at a temperature of 25-27° C. to evaporate the low boiling point organic solvent to obtain the resultant microcapsules of biocide, separating and washing the resultant product with water followed by drying at a temperature ranging between 25-35° C. to obtain the desired controlled particle size of polymer microcapsules, wherein the polymer is selected from the group consisting of a polystyrene polymer, a polystyrene copolymer, and a poly(methyl methacrylate) polymer.

2. The process as claimed in claim 1, wherein the organic phase used is prepared by dissolving polymer in a water immiscible, low boiling organic solvent.

3. The process as claimed in claim 1, wherein the low boiling organic solvent used for preparing an organic phase is selected from the group consisting of dichloromethane, chloroform and ethyl acetate.

4. The process as claimed in claim 1, wherein the concentration of polymer used in organic phase is in the range of 3 to 20 w/v %.

5. The process as claimed in claim 1, wherein the concentration of Irgarol used in organic phase is in the range of 2 to 20 w/v %.

6. The process as in claimed in claim 1, wherein the emulsifying agent used in aqueous phase is poly (vinyl alcohol).

7. The process as claimed in claim 1, wherein the amount of emulsifying agent used in aqueous phase is in the range of 1 to 8 w/v % having degree of hydrolysis of 80-98%.

8. The process as claimed in claim 1, wherein the ratio of organic phase to aqueous phase used is in the range of 1:5 to 1:20.

9. The process as claimed in claim 1, wherein the aggregation of microcapsules obtained and presence of free biocide is avoided by adding an appropriate amount of water to the aqueous phase after complete addition of organic phase to aqueous phase.

10. The process as claimed in claim 1, wherein the polymer is a polystyrene polymer.

11. The process as claimed in claim 1, wherein the polymer is a polystyrene copolymer.

12. The process as claimed in claim 1, wherein the polymer is a poly (methyl methacrylate) polymer.

13. A process for the preparation of microcapsules comprising Zinc Pyrithione, the method comprising dispersing an organic phase containing Zinc Pyrithione either in dissolved or dispersed state in a polymer solution using a low boiling point solvent, in an aqueous phase containing an emulsifying agent; agitating the above said emulsion at a speed of 800-1200 rpm, for a period of 4-6 hrs, at a temperature of 25-27° C. to evaporate the low boiling point organic solvent to obtain the resultant microcapsules of biocide, separating and washing the resultant product with water followed by drying at a temperature ranging between 25-35° C. to obtain the desired controlled particle size of polymer microcapsules, wherein the polymer is selected from the group consisting of a polystyrene polymer, a polystyrene copolymer, and a poly(methyl methacrylate) polymer.

14. The process as claimed in claim 13, wherein the organic phase used is prepared by dissolving polymer in a water immiscible, low boiling organic solvent.

15. The process as claimed in claim 13, wherein the low boiling organic solvent used for preparing an organic phase is selected from the group consisting of dichloromethane, chloroform and ethyl acetate.

16. The process as claimed in claim 13, wherein the concentration of polymer used in organic phase is in the range of 3 to 20 w/v %.

17. The process as claimed in claim 13, wherein the concentration of Zinc Pyrithione used in organic phase is in the range of 2 to 20 w/v %.

18. The process as in claimed in claim 13, wherein the emulsifying agent used in aqueous phase is poly (vinyl alcohol).

19. The process as claimed in claim 13, wherein the amount of emulsifying agent used in aqueous phase is in the range of 1 to 8 w/v % having degree of hydrolysis of 80-98%.

20. The process as claimed in claim 13, wherein the ratio of organic phase to aqueous phase used is in the range of 1:5 to 1:20.

21. The process as claimed in claim 13, wherein the aggregation of microcapsules obtained and presence of free biocide is avoided by adding an appropriate amount of water to the aqueous phase after complete addition of organic phase to aqueous phase.

22. The process as claimed in claim 13, wherein the polymer is a polystyrene polymer.

23. The process as claimed in claim 13, wherein the polymer is a polystyrene copolymer.

* * * * *